United States Patent
Kreuzer

(10) Patent No.: US 12,257,076 B2
(45) Date of Patent: Mar. 25, 2025

(54) APPARATUS, WHICH IS INSERTABLE INTO AN EAR CANAL, FOR DETECTING PHYSIOLOGICAL PARAMETERS

(71) Applicant: Cosinuss GmbH, Munich (DE)

(72) Inventor: Johannes Kreuzer, Munich (DE)

(73) Assignee: Cosinuss GmbH, Munich (DE)

( * ) Notice: Subject to any disclaimer, the term of this patent is extended or adjusted under 35 U.S.C. 154(b) by 558 days.

(21) Appl. No.: 17/604,413

(22) PCT Filed: Apr. 16, 2020

(86) PCT No.: PCT/EP2020/060699
§ 371 (c)(1),
(2) Date: Jan. 14, 2022

(87) PCT Pub. No.: WO2020/212483
PCT Pub. Date: Oct. 22, 2020

(65) Prior Publication Data
US 2022/0142575 A1 May 12, 2022

(30) Foreign Application Priority Data
Apr. 16, 2019 (DE) .................. 10 2019 205 497.8

(51) Int. Cl.
*A61B 5/00* (2006.01)
*H04R 1/10* (2006.01)

(52) U.S. Cl.
CPC ......... *A61B 5/6817* (2013.01); *H04R 1/1016* (2013.01); *H04R 1/1075* (2013.01); *A61B 2560/0406* (2013.01)

(58) Field of Classification Search
CPC .......... A61B 5/6817; A61B 2560/0406; A61B 2560/0462; A61B 5/02055;
(Continued)

(56) References Cited

U.S. PATENT DOCUMENTS 10,660,792 B2 * 5/2020 Smith .................. A61F 7/12
2002/0035340 A1 3/2002 Fraden
(Continued)

FOREIGN PATENT DOCUMENTS

DE    10 2011 081 815 A1    12/2012

OTHER PUBLICATIONS

International Preliminary Report on Patentability for International App. No. PCT/EP2020/060699 issued Sep. 28, 2021.
(Continued)

*Primary Examiner* — Jonathan T Kuo
(74) *Attorney, Agent, or Firm* — TMB Law; Timothy M. Brown

(57) ABSTRACT

The invention relates to an apparatus for recording physiological parameters, which can be inserted in an ear canal. The apparatus is designed with a tube, which is to be introduced into the ear canal, and a housing, which is connected to the tube. The tube comprises a largely cylindrical portion at a distal end that faces toward the eardrum when being worn. At least one sensor device for recording physiological parameters is integrated in the housing. The largely cylindrical portion is designed with at least one sensor opening for at least one sensor component for recording physiological parameters. The at least one sensor opening is spaced apart from the longitudinal axis $L_A$ of the largely cylindrical portion by a distance $l_{sensoropening}$. A receiver device for outputting sound signals may also be integrated in the apparatus, so that the apparatus is suitable for applying sound to the eardrum. The invention further relates to an ear adapter for detachable attachment to the largely cylindrical portion of the tube of the apparatus, wherein the ear adapter is attached thereto in such a way that the at least one sensor opening comes to lie in close
(Continued)

proximity to an inner surface of the ear canal or comes into contact therewith.

13 Claims, 5 Drawing Sheets

(58) Field of Classification Search
CPC ............ A61B 5/02427; A61B 5/14552; H04R 1/1016; H04R 1/1075
See application file for complete search history.

(56) References Cited

U.S. PATENT DOCUMENTS

| | | |
|---|---|---|
| 2005/0209516 A1 | 9/2005 | Fraden |
| 2009/0177097 A1* | 7/2009 | Ma .......................... G05B 15/02 600/500 |
| 2014/0187885 A1* | 7/2014 | Kreuzer ................. A61B 5/741 600/300 |
| 2017/0339480 A1 | 11/2017 | Lee et al. |
| 2018/0008457 A1* | 1/2018 | Smith .................... A61N 2/006 |
| 2018/0113673 A1 | 4/2018 | Sheynblat |
| 2018/0220903 A1* | 8/2018 | LeBoeuf ............ A61B 5/14546 |
| 2021/0006885 A1 | 1/2021 | Austen |

OTHER PUBLICATIONS

International Search Report for Int. App. No. PCT/EP2020/060699 issued Jul. 10, 2020.
International Search Report for international application No. PCT/EP2022/067163 issued Sep. 28, 2022.
Written Opinion for international application No. PCT/EP2022/067163 issued Sep. 28, 2022.

* cited by examiner

APPARATUS, WHICH IS INSERTABLE INTO AN EAR CANAL, FOR DETECTING PHYSIOLOGICAL PARAMETERS

TECHNICAL FIELD

The invention relates to an apparatus for recording physiological parameters, according to the subject matter of claim 1.

PRIOR ART

Apparatuses for recording physiological parameters, which can be inserted in an ear canal, are known from the prior art. Apparatuses for applying sound to the eardrum are also known. Such apparatuses are, for example, wearable hearing apparatuses for treating people with hearing loss and/or for listening to music and/or apparatuses to be worn in the ear for determining body temperature, heart rate or heart rate variability.

Apparatuses known from the prior art which are to be placed in the ear canal for recording physiological parameters (for example EP 2 717 756 B1) use, for example, optical measuring methods to record the pulse rate or the arterial oxygen saturation (pulse oximetry). Light emitted by monochromatic light-emitting diodes (LEDs) or laser diodes passes through the tissue and is received by a photodiode. The oxygen saturation can be determined from the different absorption of oxygen-saturated (arterial) blood compared to oxygen-poor (venous) blood at defined wavelengths. With such measurements, meaningful measurement results can only be achieved if the relevant sensors (for example light-emitting diodes or laser diodes, photodiode, infrared sensor) are optimally positioned in the ear canal in direct contact with the inner wall of the ear canal. In addition, pulse oximetry or pulse rate measurement requires a positioning that does not change or that changes only slightly while the sensor is being worn. In this case, the sensors are conventionally integrated in a so-called "dome" ("sensor element attachment") in order to ensure optimal contact with the wall of the wearer's ear canal. The sensors located in the dome are electrically contacted and are actuated from elsewhere. Since the reading-out and digitization of the data likewise take place elsewhere, there are usually multiple electrical connections between the sensors located in the dome and evaluation electronics.

In the case of apparatuses for applying sound to the eardrum (for example in the case of hearing aids), a distinction is made between different designs, such as for example Behind-The-Ear hearing aids (BTE), hearing aids with external receivers (Receiver-In-the-Canal devices, RIC) and In-The-Ear hearing aids (ITE), the latter being subdivided into different subgroups (In-The-Ear, ITE; In-The-Canal, ITC; Completely-In-the-Canal, CIC, Invisible-In-the-Canal, IIC) depending on the depth of the position in the ear canal. As basic components, hearing aids comprise a sound receiver (input transducer, microphone), an amplifier (analog amplifier, digital signal processor) and a miniature loudspeaker (output transducer, receiver) for transmitting the sound signals to the eardrum. The sound is routed to the eardrum either by means of an earmold (earpiece), for example in the case of ITE hearing aids, or by means of a slim tube with an open endpiece ("dome"), for example in the case of BTE hearing aids. Such domes usually have one or more rings curved like a dome, which hold the dome in the ear canal. Domes known from the prior art (for example EP 2 360 947 A2) are exchangeable, i.e. they can be plugged onto the end of a sound tube or onto an ITE loudspeaker and can be removed therefrom, for example for adaptation to an individual size of the ear canal or for cleaning purposes.

In the case of a combined apparatus for applying sound to the eardrum and for recording physiological parameters, which can be inserted in an ear canal, it is necessary on the one hand for the earpiece that is to be inserted in the ear canal to be made exchangeable, for example for adaptation to an individual size of the ear canal or for cleaning purposes, and on the other hand to ensure the reliable and precise measurement of the physiological parameters by optimally positioning the relevant sensors in the ear canal in close contact with the wall of the ear canal. Sensors arranged in the dome may for example be connected to the evaluation electronics via electrical plug-in connections.

Disadvantageously, such electrical plug-in connections, which are greatly miniaturized for arrangement in the ear canal, are very cost-intensive; in addition, from a technical point of view, these connections can be protected against moisture and water only with difficulty.

The problem addressed by the present invention is therefore that of providing an apparatus for recording physiological parameters, which is optimally adapted to the individual anatomical conditions of a wearer's ear canal and which enables the reliable, precise measurement of physiological parameters. The apparatus is intended to be able to be used multiple times and is intended to be able to be manufactured in a cost-effective manner. In particular, that problem addressed by the present invention is that of providing a multifunctional apparatus which can be inserted in an ear canal and which is designed to apply sound to the eardrum and/or to record physiological parameters. In the apparatus according to the invention, the intention is also for components, in particular the ear adapter, to be exchangeable in an easy and cost-effective manner for adaptation and/or cleaning purposes.

PRESENTATION OF THE INVENTION

In a first aspect, the present invention therefore relates to an apparatus for recording physiological parameters, which can be inserted in an ear canal, comprising a tube, which is to be introduced into the ear canal, and a housing, which is connected to the tube. At least one sensor device for recording a physiological parameter is integrated in the housing. The tube may either be designed integral with the housing or may be detachably connected thereto via a form-fitting and/or friction-fitting connection. By way of example, the tube may be arranged with the housing via a latching connection or a rotary connection. The tube comprises a largely cylindrical portion at a distal end that faces toward the eardrum when being worn. Here, the expression "largely cylindrical" refers to a structure in the form of a general cylinder, in particular a hollow cylinder. A cylinder base of said portion is designed as a closed, flat curve and according to the invention is not subject to any restrictions with regard to its shape; by way of example, it may be designed as an ellipse or circle. At the largely cylindrical portion of the distal end, the tube is designed with at least one sensor opening for at least one sensor component for recording physiological parameters. In connection with the apparatus according to the invention, the term "distal" refers to the distance in the direction of the user's eardrum relative to the at least one sensor device of the apparatus, which is integrated in the housing. In the case of a BTE apparatus, the cylindrical portion is, for example, distal in relation to the receptacle of the housing, which is located behind the ear and in which the sensor device and optionally additional components (for example charging device) are arranged. The at least one sensor opening is thus arranged at the distal end facing toward the eardrum and at a distance from the sensor device since, when the apparatus according to the invention is being worn, the distal end of the tube accordingly comes to lie adjacent to the wearer's eardrum. The at least one sensor opening of the apparatus according to the invention is designed as an opening in the distal end of the tube for accommodating at least one sensor component; depending on the dimensioning of the sensor component relative to the sensor opening, it is also possible for example for two or more such sensor components to be arranged in the opening. By way of example, a photodiode and an LED may be arranged in a sensor opening, wherein in this case an optical barrier is advantageously arranged between the sensor components in order to accurately record the physiological parameters (for example oxygen saturation, pulse rate). Advantageously, a sensor component, for example a photodiode or a temperature sensor, is in each case arranged in the corresponding sensor opening in such a way that the sensor component ends flush with the surface of the largely cylindrical portion. The at least one sensor opening is spaced apart from the longitudinal axis $L_A$ of the largely cylindrical portion of the tube by a distance $l_{sensoropening}$. The at least one sensor opening is arranged in such a way that, when the apparatus is being worn, the at least one sensor opening comes to lie in contact with an inner wall of the ear canal. According to the invention, by means of a single apparatus inserted in the ear canal, it is possible for two physiological parameters, for example the body temperature or the pulse rate of the wearer, to be recorded for example simultaneously via corresponding sensor components. Alternatively, one physiological parameter, such as the pulse rate of the wearer, can be recorded via functionally different sensor components, thereby increasing the reliability of the determination through redundant measured values. In the apparatus according to the invention, the at least one sensor component is fixedly installed in the tube or in the housing and is not connected to the associated at least one sensor device via a plug-on dome (as in the case of conventional apparatuses to be worn in the ear for recording physiological parameters). As a result, the apparatus according to the invention is easy to handle and does not require greatly miniaturized connectors that are to be worn in the ear canal. By way of example, cleaning can easily be carried out without having to disassemble the apparatus. This ensures that the apparatus can be reused. Advantageously, multiple functions can be provided in a single apparatus. The accordingly eccentric arrangement of the at least one sensor component in the distal end of the housing advantageously makes it possible on the one hand to arrange various components in a compact manner in the spatially delimited, distal end region of the tube, and at the same time, on account of the peripheral arrangement of the at least one sensor component in direct contact with the inner wall of the ear canal, enables optimal signal detection with few spurious signals.

In one advantageous development of the apparatus according to the invention, the at least one sensor opening may be spaced apart from the lateral surface M of the largely cylindrical portion of the tube by a distance $m_{sensoropening}$, wherein $m_{sensoropening}$ is $l_{sensoropening}$. Advantageously, for example if two sensor openings are present, one sensor opening of the two sensor openings may in relative terms lie closer to the lateral surface than to the longitudinal axis $L_A$ of the largely cylindrical portion of the tube, while another sensor opening is arranged at a different distance from the lateral surface.

In a further embodiment, the largely cylindrical portion of the distal end of the tube may be arranged with an aperture, wherein the aperture may preferably be a through-aperture. The term "through-aperture" denotes an aperture which is open "all the way through" both on the side facing toward the eardrum when being worn and on the side facing away from the eardrum when being worn. Advantageously, by means of an apparatus according to the invention, the cylindrical portion of which is arranged with a through-aperture, a physiological parameter can be recorded without hindering the onward transmission of sound in the ear canal.

In one preferred embodiment, a receiver device for outputting sound signals may be integrated in the housing so that the apparatus is designed to apply sound to the eardrum. The tube may accordingly be designed with a sound outlet opening at the distal end, wherein the sound outlet opening is spaced apart from the longitudinal axis $L_A$ of the largely cylindrical portion of the tube by a distance $l_{soundoutletopening}$. Since the distal end of the tube comes to lie adjacent to the wearer's eardrum when the apparatus according to the invention is being worn, sound waves can be transmitted directly to the eardrum. According to the invention, with regard to the longitudinal axis of the largely cylindrical portion, a sound outlet opening is positioned less eccentrically than the at least one sensor opening; this arrangement corresponds to the arrangement of the sound outlet opening in conventional hearing aids, in which the sound waves are routed to the corresponding eardrum in a largely central manner. Thus, by means of a single apparatus inserted in the ear canal, sound waves can be transmitted to the eardrum of a wearer of the apparatus and at the same time one or more physiological parameter(s) can be recorded via corresponding sensor components.

In a further embodiment, the apparatus may comprise an ear adapter for detachable attachment to the largely cylindrical portion of the end of the tube of the apparatus, wherein the ear adapter comprises a central piece for engaging in the aperture in the end of the largely cylindrical portion of the tube, an ear contact surface for engaging with an inner wall of the ear canal when being worn, and an endpiece for connecting the central piece and the ear contact surface, wherein the ear contact surface at least partially encloses the largely cylindrical portion of the end of the tube and is attached thereto in such a way that, when the apparatus is being worn, the at least one sensor opening comes to lie in close proximity to an inner wall of the ear canal. In one particularly preferred embodiment, the ear contact surface may be arranged on the largely cylindrical portion of the end of the tube in such a way that, when the apparatus is being worn, the at least one sensor opening comes to lie in contact with an inner wall of the ear canal. According to the invention, the term "ear adapter" will be understood to mean a flexible earpiece made of a flexible material, which is not individually adapted to a user but adapts to the shape of the ear canal on account of the material properties. By way of example, such an ear adapter approximately corresponds to the "dome" (earpiece) of conventional hearing aids, the ear adapter according to the invention differing from the conventional, flexible "earpieces" in that it is attached to the end of the corresponding portion of the tube in such a way that, when the apparatus is being worn, the at least one sensor opening at the distal end of the tube comes to lie in close proximity to or in contact with an inner wall of the ear canal. The expression "detachable attachment" will be understood to mean the friction-fitting and/or form-fitting connection of the ear adapter to the distal end of the housing; advantageously, the central piece of the ear adapter and the aperture in the distal end of the housing may be designed in a manner complementary to one another, so that the friction-fitting and/or form-fitting connection between the largely cylindrical portion of the distal end of the tube and the ear adapter is formed both by the engagement of the central piece in the aperture in the largely cylindrical portion of the distal end of the tube and by the engagement of the ear contact surface with the largely cylindrical portion of the end of the tube. The connection may optionally be secured by suitable fasteners to prevent unintentional detachment. The ear adapter according to the invention on the one hand enables easy adaptation to the ear canal of the wearer of the apparatus, for example by different dimensioning of the ear contact surface, and on the other hand enables one or more sensor components arranged in the corresponding sensor openings to lie in close proximity to or in direct contact with the inner wall of the ear canal (by accordingly pressing the corresponding sensor opening against the wall of the ear canal), thereby enabling the accurate recording of physiological parameters with little interference. In use, an ear adapter that completely encompasses the largely cylindrical portion of the distal end of the tube may be made of a transparent material in the region of the at least one sensor opening, for example in the region of the ear contact surface, and/or may have a much smaller thickness, for example in the region of the ear contact surface, compared to the side of the ear adapter facing away from the sensor opening. Furthermore, the detachably attached ear adapter can thus be plugged onto the largely cylindrical portion of the distal end of the tube in the sense of a plug-in connection, thereby enabling easy exchange in the event of soiling (for example by cerumen). On the other hand, a receiver device installed in the tube and housing and/or the at least one sensor device and the associated at least one sensor component likewise installed in the housing can easily be cleaned without having to remove the electronic components beforehand. Furthermore, the ear adapter can close the ear canal in relation to sound waves, i.e. can reduce the permeability thereof to sound.

In one preferred implementation of the apparatus according to the invention, a receiver device for outputting sound signals and at least one sensor device for recording physiological parameters may be designed as an integral component. In an alternative implementation, at least two sensor devices for recording physiological parameters may be designed as an integral component. Different combinations of receiver device and sensor device(s) can thus easily be installed in the apparatus according to the invention, for example a receiver device combined with a PPG sensor (photoplethysmography sensor) and/or an acceleration sensor or a receiver device combined with a temperature sensor and/or infrared sensor. The manufacturing costs of the apparatus can thus advantageously be reduced, while achieving the greatest possible flexibility with regard to the recorded physiological parameters.

In one preferred development of the apparatus according to the invention, the tube may be designed integral with the housing. While the ability to separate the tube from the housing enables easy integration of the at least one sensor device and of the at least one sensor component, for example in existing apparatuses for applying sound to the eardrum (hearing aids, headphones for listening to music), the integral design ensures easy handling, for example during insertion/removal or when cleaning the apparatus according to the invention.

In a further embodiment of the apparatus according to the invention, the largely cylindrical portion at the distal end of the tube may be designed with a convexly curved lateral surface. The convex curvature of the lateral surface provides more space and thus makes it possible to arrange multiple components (receiver, multiple sensor components) in the distal end of the tube. In the case of a narrow ear canal (for example in children), it is also much easier to press the sensor component, arranged in the at least one sensor opening, against the inner wall of the ear canal. Furthermore, the convex curvature of the lateral surface enables improved fastening of the attached ear adapter in the sense of an improved form fit of the plug-in connection between the ear adapter and the distal end of the tube. In one advantageous development, the ear contact surface of the ear adapter may be designed with a shape that is largely complementary to the largely cylindrical portion of the distal end of the tube. By way of example, the ear adapter with its ear contact surface may likewise have a largely cylindrical shape, the cylinder being cut along its longitudinal axis such that the at least one sensor opening is open toward an inner surface of the ear canal when the ear adapter is plugged on. The ear adapter may thus be designed as a cylinder segment; the ear adapter may advantageously be designed as a partially hollow cylinder segment with a convexly curved lateral surface. Alternatively, the ear adapter may be designed as a cylinder with a convexly curved lateral surface, the ear contact surfaces along the lateral surfaces being designed with a different thickness such that the thickness in the region of the at least one sensor opening is smaller than in the region remote from the at least one sensor opening.

In one particularly preferred embodiment of the apparatus according to the invention, the longitudinal axis Lo of the ear adapter may be spaced apart from the longitudinal axis $L_A$ of the largely cylindrical portion of the distal end of the tube. The ear adapter is thus arranged eccentrically in relation to the longitudinal axis of the largely cylindrical distal end of the tube. The at least one sensor component arranged in the corresponding at least one sensor opening is thus stabilized in the ear canal and is optimally positioned against the inner wall of the ear canal for recording physiological parameters with little interference.

In a further, particularly preferred development of the apparatus according to the invention, an end face of the largely cylindrical portion of the distal end of the tube may have a radius $R_A$, and the endpiece of the ear adapter may be designed as a circle or circular segment with radius $R_O$, wherein $R_A < R_O$ and the distance a between the center points $M_A$, $M_O$ of the end faces is $0 < a < R_O$. Here, $M_A$ denotes the center point of an end face of the largely cylindrical portion of the distal end of the tube, and $M_O$ denotes the center point of the endpiece of the ear adapter, which is designed as a circle or circular segment with radius $R_O$. The ear adapter is thus arranged eccentrically in relation to an end face of the largely cylindrical distal end of the tube. The at least one sensor component arranged in the corresponding sensor opening is thus stabilized in the ear canal and is optimally positioned against the inner wall of the ear canal for recording physiological parameters with little interference.

In a further embodiment of the apparatus according to the invention, the sound outlet opening may be arranged largely centrally in an end face of the largely cylindrical portion of the distal end of the tube. Advantageously, if the sound outlet opening is arranged largely centrally, use can be made of hearing aid designs that already exist, in which at least one sensor opening containing at least one sensor device and the corresponding at least one sensor component can be integrated.

In a further preferred embodiment, the sound outlet opening may be adapted to accommodate a cerumen filter device. This is particularly advantageous if the apparatus is based on already known designs for hearing aids.

In one preferred development of the apparatus, the central piece of the ear adapter may be designed with a through-aperture. The term "through-aperture" will be understood to mean an aperture which is open both on the side facing toward the endpiece and on the side facing away from the endpiece. As an alternative or in addition, the ear adapter may be designed with at least one ear adapter opening, wherein the at least one ear adapter opening may be formed in the region of the end face or at the transition between the end face and the ear contact surface of the ear adapter. An ear adapter comprising a central piece designed in this way and/or an ear adapter opening designed in this way enables undisturbed sound transmission, for example in an apparatus with no receiver function or with a limited receiver function. Furthermore, easy attachment and exchange of the ear adapter can take place by means of a tool designed in a manner complementary to the aperture of the ear adapter.

In one preferred development of the apparatus according to the invention, the largely cylindrical portion at the distal end of the housing may be made of a harder material than the ear adapter, wherein the ear adapter may comprise a material comprising a plastic, a rubber, a silicone and/or an elastomer. Forming the ear adapter from a material that has elastic properties advantageously enables an improved connection between the distal end and the ear adapter by way of a friction fit.

As used here, the singular form of the article "a" or "the" encompasses the corresponding plural forms, unless stated otherwise. By way of example, the expression "an ear contact surface" encompasses one such ear contact surface or multiple ear contact surfaces.

The invention will be explained in greater detail below, by way of example, on the basis of the accompanying schematic drawings. The drawings are not true to scale; in particular, for reasons of clarity, the ratios of the individual dimensions to one another do not necessarily correspond to the ratios of the dimensions in actual technical implementations.

Several preferred exemplary embodiments will be described, but the invention is not limited to these. In principle, any variant of the invention described or implied in the context of the present application may be particularly advantageous, depending on the economic, technical and optionally medical requirements in each case. Unless stated otherwise, and insofar as is technically feasible in principle, individual features of the described embodiments are interchangeable or can be combined with one another and also with features known per se from the prior art.

BRIEF DESCRIPTION OF THE FIGURES

FIG. 2B shows this arrangement in a further view, while

PREFERRED WAY OF IMPLEMENTING THE INVENTION

Elements that correspond to one another are in each case provided with the same reference signs in the figures.

Figure 1:
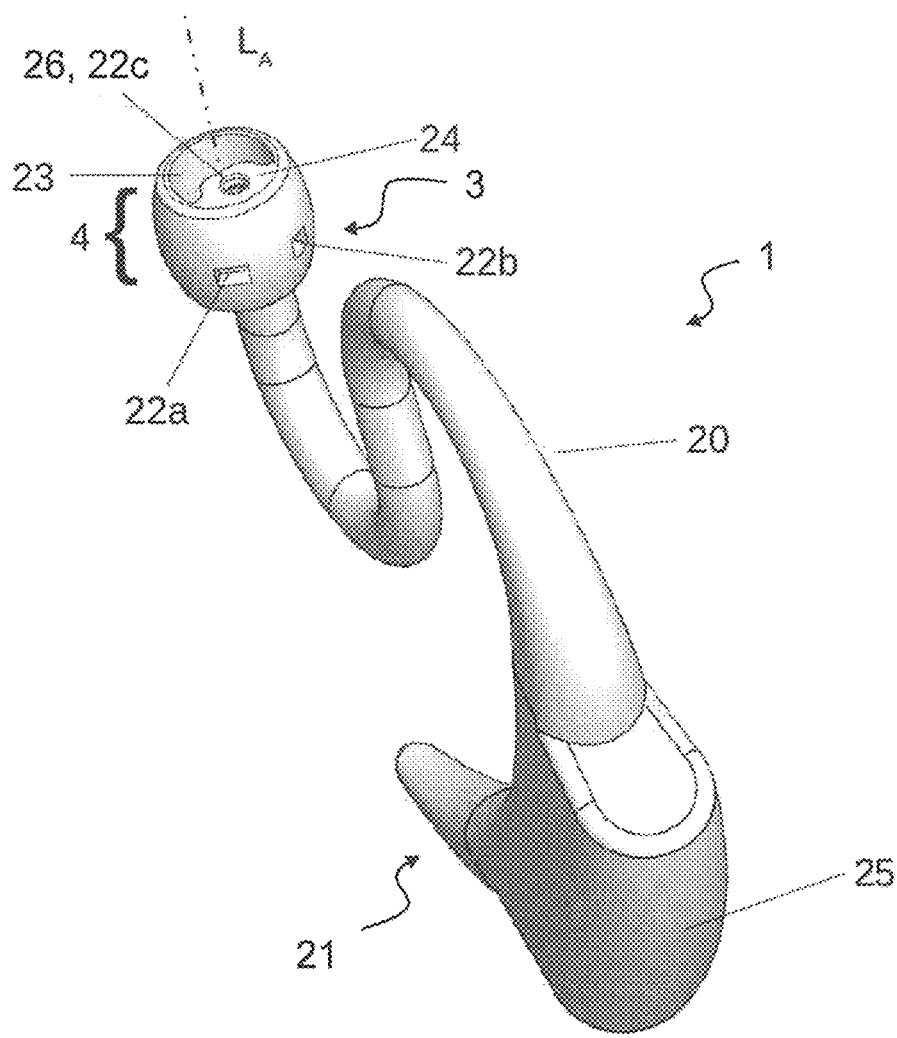
FIG. 1 shows an exemplary embodiment of the apparatus according to the invention in an oblique view from above, wherein a largely cylindrical portion of the distal end of the tube is designed with one sound outlet opening and two sensor openings.

FIG. 1 shows an exemplary embodiment of the apparatus (1) according to the invention in an oblique view from above, the apparatus here being designed as a BTE (Behind-The-Ear) apparatus. The apparatus is designed to be inserted in an ear canal of the user and comprises a tube (20), which is to be introduced into the ear canal of the user, and a housing (21), which is connected to the tube (20) and has a receptacle (25), the interior of which (not shown) is designed to accommodate various components, for example electronic, micromechanical or optical components. By way of example, a receiver device for outputting sound signals and/or at least one sensor device for recording physiological parameters may be accommodated in the receptacle (25). The apparatus further has a distal end (3) of the tube (20), wherein the term "distal", as used herein, refers to the distance in the direction of the eardrum of the user relative to the sensor device of the apparatus, which is integrated in the housing (21). In the case of a BTE (Behind-The-Ear) apparatus, the sensor device is located in the receptacle (25) of the housing (21), which comes to lie behind the ear when the apparatus is being worn; the distal end (3) is accordingly arranged in the direction of the eardrum. Extending between the receptacle (25) and the distal end (3) of the housing (21) is the tube (20), which may be designed as a plug-on, slim tube element or else as an S-shaped connecting element integral with the housing (21) and the receptacle (25) formed therein, as shown in FIG. 1. By way of example, an optimal bracing of the apparatus in defined anatomical structures of the outer ear can be ensured by a flexible, S-shaped structure. The distal end (3) of the tube (20) is arranged with a largely cylindrical portion (4), which has a larger diameter than the tube (20). The largely cylindrical portion (4) shown is designed with a largely circular base and convexly curved lateral surfaces. In the exemplary embodiment shown, the portion has one sound outlet opening (26) and two sensor openings (22a, 22b). The sound outlet opening (26) is arranged in a distal end face (24) of the largely cylindrical portion (4) of the tube (20), while the illustrated sensor openings (22a, 22b) are located in the convexly curved lateral surface of the portion (4). As an alternative to the sound outlet opening (26), the opening arranged in the distal end face (24) of the largely cylindrical portion (4) of the tube (20) may also be a further sensor opening (22c), for example for accommodating an infrared sensor, by means of which the body temperature can be recorded via an infrared emission of the eardrum. Therefore, once the apparatus shown has been inserted in an ear canal of the wearer, the sound outlet opening (21) is oriented in the direction of the user's eardrum, which is located at the end of the ear canal, while the two sensor openings (22a, 22b) come to lie in close proximity to the inner wall of the ear canal. The sensor openings (22a, 22b) stabilize the sensor components (not shown) arranged therein for recording physiological parameters, for example the body temperature and/or the pulse rate of the user, and ensure contact thereof with the inner wall of the ear canal. The sound outlet opening (26) and the two sensor openings (22a, 22b) are spaced apart from the longitudinal axis $L_A$ (dashed line) of the largely cylindrical portion (4) of the housing (2) by a distance $l_{soundoutletopening}$ and a distance $l_{sensoropening}$, respectively. The largely cylindrical portion (4) of the distal end (3) of the tube (20) is additionally designed with an aperture (23). A through-aperture (23) (i.e. an aperture that is open toward both cylinder bases) can ensure the transmission of sound waves to the eardrum even when the apparatus is inserted in the ear canal.

Figure 2A:
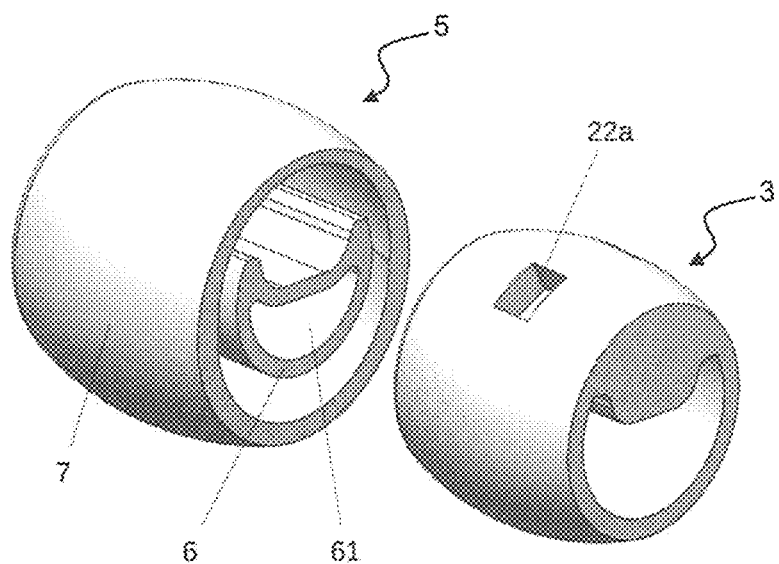
FIG. 2A shows a detail view of the largely cylindrical portion of the distal end of the tube of the apparatus according to the invention, wherein an ear adapter is separate from the largely cylindrical portion of the distal end of the tube.
Figure 2B:
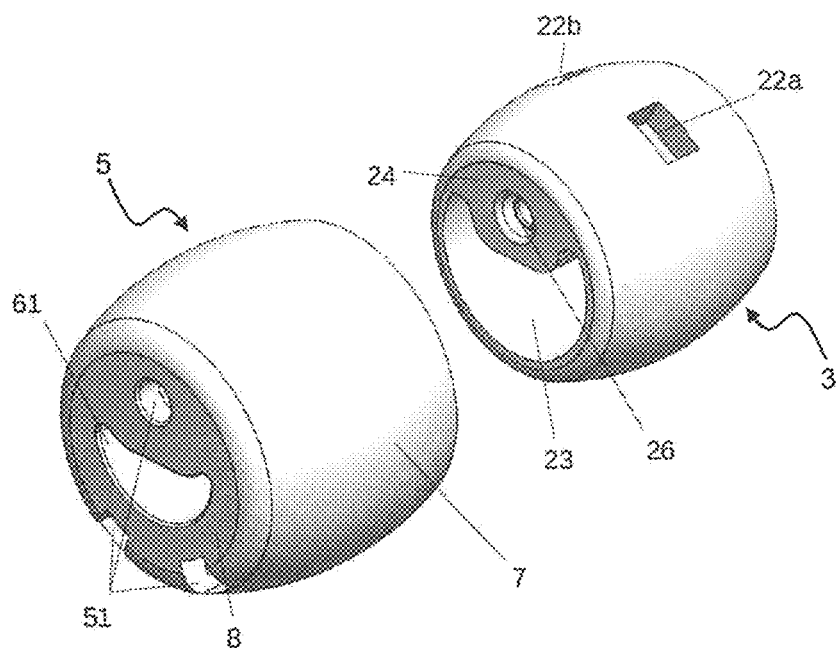
Figure 2C:
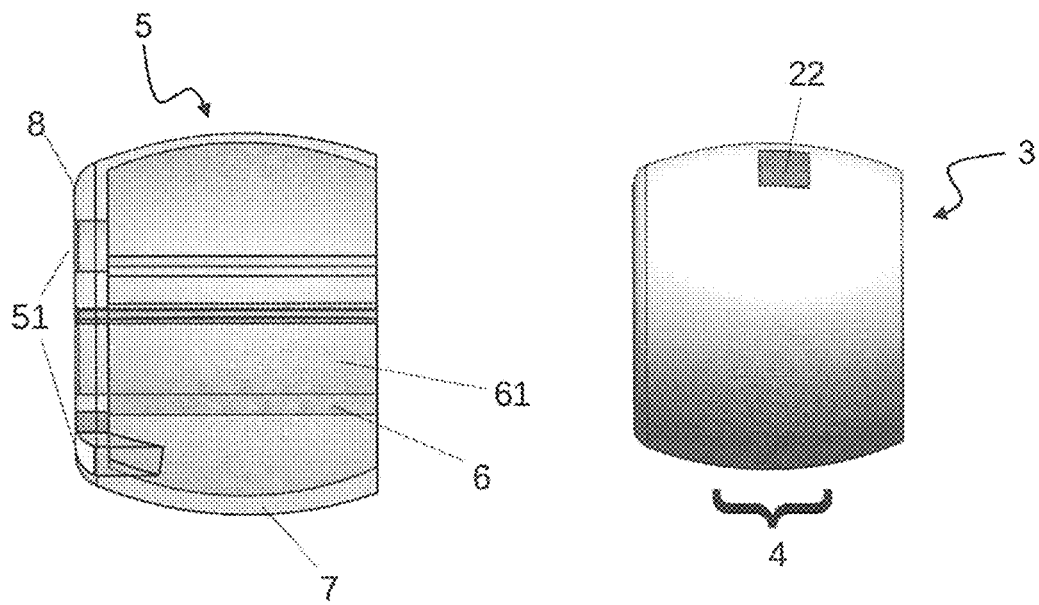
FIGS. 2C and 2D show a view from the side with a cross-sectional view of the ear adapter (FIG. 2C) and a partially transparent plan view of the largely cylindrical portion of the distal end of the tube with the ear adapter plugged thereon (FIG. 2D).
Figure 2D:
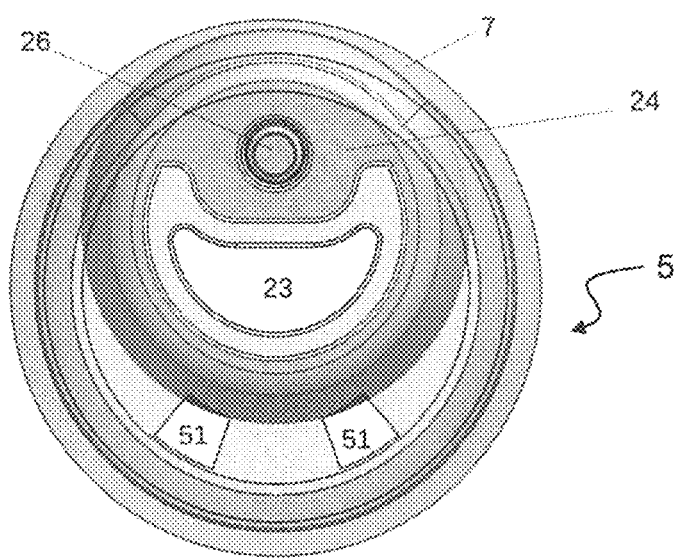

FIG. 2A to FIG. 2C each show a detail view of the largely cylindrical portion (4) of the distal end (3) of the tube (20) of the apparatus according to the invention with an ear adapter (5), wherein the latter is separate from the portion (4) of the distal end (3) of the tube (20) (FIGS. 2A-2C). The distal end (3) is designed with two sensor openings (22a, 22b) and with one sound outlet opening (26), which is arranged in the distal end face (24) of the housing. It is clear that the sensor openings (22a, 22b) are each spaced apart from the lateral surface M of the largely cylindrical portion (4) by a distance $m_{sensoropening}$, wherein $m_{sensoropening}$ is $l_{sensoropening}$. In the case shown, the sensor openings are located directly in the lateral surface of the largely cylindrical portion (4). Furthermore, the distal end (3) of the tube (2) has an aperture (23). This aperture (23) is arranged to engage with a central piece (6) of the ear adapter (5). The central piece (6) of the ear adapter (5) is designed with a through-aperture (61), the aperture (61) being open toward the endpiece (8) and toward the side facing away from the endpiece (8), so that a continuous space is created. As shown, the ear adapter (5) has a shape that is largely complementary to the largely cylindrical portion (4) of the distal end (3) of the tube (20): the central piece (6) comes to lie in the aperture (23), while the ear contact surfaces (7) engage around the portion (4) so that the sides of the ear contact surfaces (7) facing toward the central piece (6) come to lie on the convexly curved lateral surface of the portion (4) and the sides of the ear contact surfaces (7) facing away from the central piece (6) come to lie on the inner wall of the ear canal. The central piece (6) and the ear contact surfaces (7) are connected by the endpiece (8). The ear adapter (5) is additionally designed with openings (51), which here are arranged at the transition between the endpiece (8) and the ear contact surfaces (7) and in the region of the sound outlet opening (26). Together with the aperture (61) arranged in the central piece (6), the openings (51) enable the transmission of sound waves to the eardrum when the apparatus is inserted in the ear canal. Advantageously, the largely cylindrical portion (4) at the distal end (3) of the housing (2) may be made of a harder material than the ear adapter (5). Advantageously, the ear adapter (5) is made of a flexible material, for example of silicone, as a result of which the form-fitting connection of the ear adapter (5) to the portion (4) is additionally improved by a friction fit. The cross-sectional view of the ear adapter (5), shown in FIG. 2C, illustrates that the ear contact surface (7) of the ear adapter (5) has a much smaller wall thickness in the region that comes to lie in the region of the sensor opening (22) of the largely cylindrical portion (4) during use than in the region that does not come to lie in the region of the sensor opening (22) during use. This relationship is illustrated once again in FIG. 2D, which shows the largely cylindrical portion (4) with the ear adapter (5) plugged thereon, the ear adapter being shown as partially transparent for the sake of better comprehension.

Figure 3A:
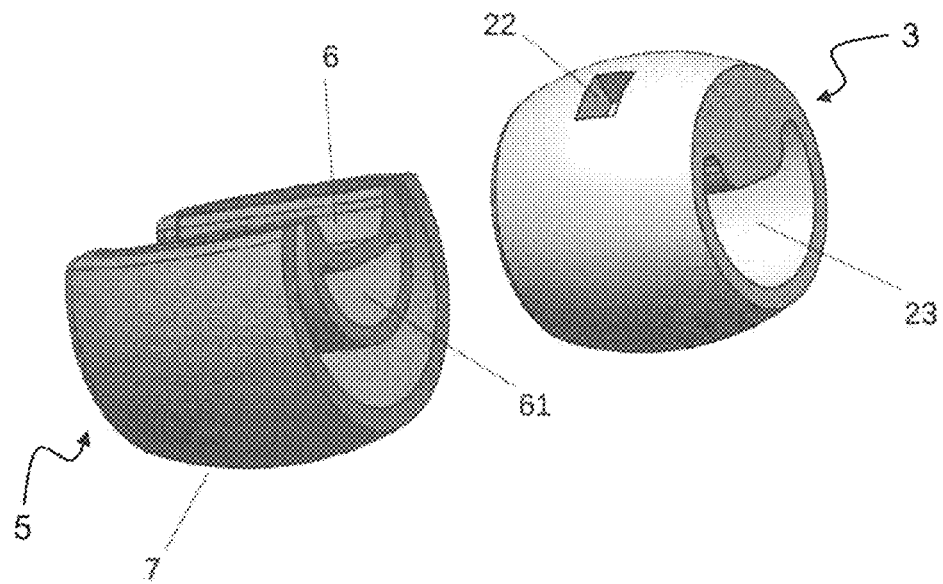
FIG. 3A shows a detail view of the distal end of the apparatus according to the invention in a further embodiment.
Figure 3B:
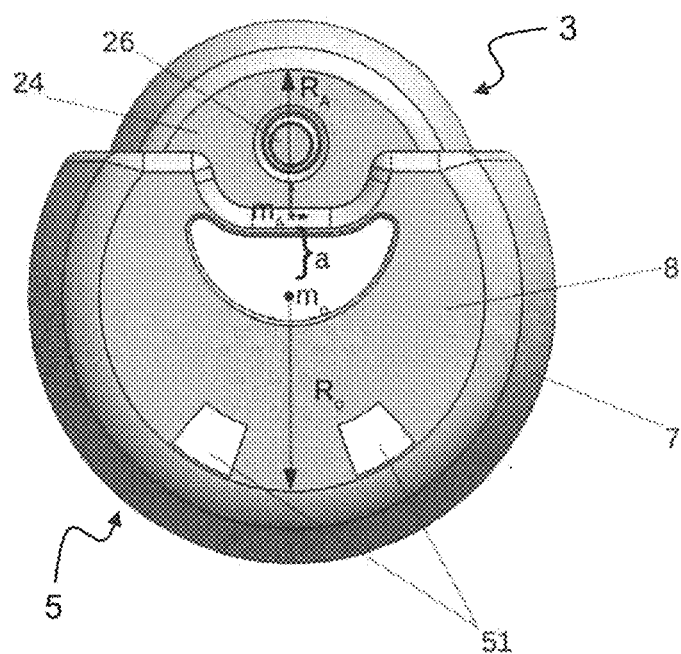
FIG. 3B shows a plan view of the largely cylindrical portion at the distal end of the apparatus according to the invention with the ear adapter plugged thereon.

FIG. 3A shows a detail view of the distal end of the apparatus according to the invention in a further embodiment. The central piece (6) of the ear adapter (5) is designed with a through-aperture (61), the aperture (61) being open toward the endpiece (8, not shown in the perspective view) and toward the side facing away from the endpiece (8), so that a continuous space is created. The ear adapter (5) can engage in the corresponding aperture (23) of the largely cylindrical portion (4) of the distal end (3) of the tube (20). The plan view, shown in FIG. 3B, of the distal end of the apparatus according to the invention with the ear adapter (5) plugged thereon illustrates the eccentric arrangement of the ear adapter (5). The end face (24) of the largely cylindrical portion (4) of the distal end (3) of the tube (20) has a radius $R_A$, while the endpiece (8) of the ear adapter (5) is designed as a circular segment with radius $R_O$. If $R_A<R_O$, the distance a between the center points $M_A$, $M_O$ of the end faces (24, 8) is $0<a<R_O$. Here, $M_A$ denotes the center point of the end face (24) of the largely cylindrical portion (4) of the distal end (3) of the tube (20), and $M_O$ denotes the center point of the endpiece (8) of the ear adapter (5), which is designed as a circular segment with radius $R_O$. The ear adapter (5) is thus arranged eccentrically in relation to an end face of the largely cylindrical distal end of the tube. As shown here, the ear contact surface (7) of the ear adapter (5) only partially encloses the largely cylindrical portion (4); the ear adapter (5), which is designed in a manner complementary to the largely cylindrical portion (4), is thus designed as a cylinder segment. According to the invention, the ear adapter (5) is eccentric in relation to the largely cylindrical portion (4) so that, during use, at least one sensor opening (shown in FIG. 3A: 22) can come into contact with an inner wall of the ear canal. The sensor component arranged in the sensor opening and stabilized by the latter is advantageously pressed against the inner wall of the ear canal by the eccentrically arranged ear adapter (5) and thus enables an improved signal quality. It is clear from FIG. 3A that, on account of the through-aperture (61) of the central piece (6) of the ear adapter (5), the apparatus inserted in an ear canal of the wearer does not close off this canal in a manner impermeable to sound since sound waves can reach the wearer's eardrum through said opening. One or more additional openings (51) of the ear adapter (5) may be arranged at the transition from the endpiece (8) thereof to the ear contact surface (7) and may thus enable a further permeability to sound (view in FIG. 3B). This arrangement is particularly advantageous if the apparatus according to the invention is designed with multiple sensor devices for recording various physiological parameters, for example for recording body temperature, pulse rate, oxygen saturation, etc. The sensor devices may in this case be installed integrally in a component/assembly.

Figure 4A:
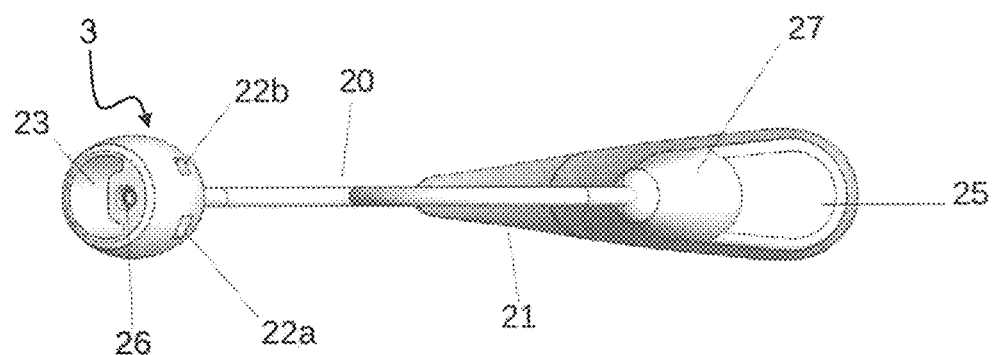
FIGS. 4A to 4C show a further exemplary embodiment of the apparatus according to the invention, in a plan view without the ear adapter plugged thereon (FIG. 4A), in an oblique view from below with the ear adapter plugged thereon (FIG. 4B), and in a plan view (FIG. 4C).
Figure 4B:
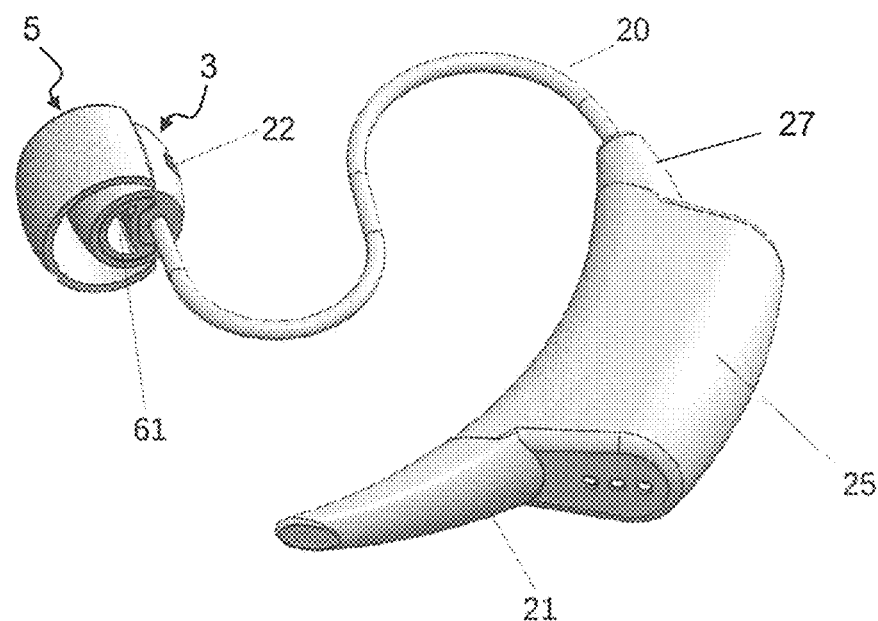
Figure 4C:
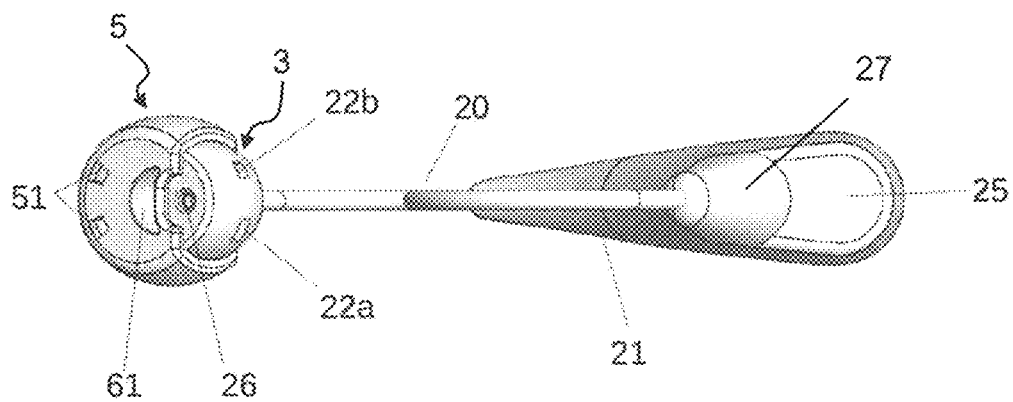

FIGS. 4A to 4C show a further exemplary embodiment of the apparatus according to the invention in the form of a BTE apparatus. FIG. 4A shows the apparatus without the ear adapter plugged thereon in a plan view, while FIGS. 4B and 4C show the apparatus with the ear adapter plugged thereon in an oblique view from below and in a plan view (FIG. 4C).

The tube (20) is connected to the housing (21) in the region of the receptacle (25) via a plug-in connection (27). The tube (20) is designed as a flexible, preferably transparent tube of small cross-section, which serves to guide the relevant leads into the largely cylindrical portion (4) of the distal end (3). A tube (20) of such design is used for example in conventional BTE hearing aids and is advantageously only slightly visible when the apparatus is being worn. The sensor devices and receiver devices accommodated in the receptacle (25) of the housing (21) end in corresponding contacts in the region of the plug-in connection (27); the leads extending in the tube (20) end in complementary contacts on the plug-in connector side and in corresponding sensor components or loudspeaker components in the region of the largely cylindrical portion.

LIST OF REFERENCE SIGNS 1 apparatus for applying sound to the eardrum and/or for recording physiological parameters
20 tube
21 housing
22 sensor opening, portion 4
23 aperture, portion 4
24 end face, portion 4
25 receptacle in housing
26 sound outlet opening
27 plug-in connection
3 distal end of the tube
4 largely cylindrical portion
5 ear adapter
51 opening in ear adapter
6 central piece
61 aperture in central piece
7 ear contact surface
8 endpiece

The invention claimed is:

1. An apparatus for recording physiological parameters, which can be inserted in an ear canal, comprising:
a) a tube adapted to be introduced into an ear canal; and
b) a housing connected to the tube, wherein the housing has integrated therein at least one sensor device adapted to record a physiological parameter;
wherein the tube comprises a largely cylindrical portion at a distal end of the tube, wherein the largely cylindrical portion is adapted to face toward an eardrum of a user when the apparatus is inserted in an ear canal;
wherein the largely cylindrical portion of the distal end of the tube includes an aperture and at least one sensor opening for the at least one sensor device that is adapted to record a physiological parameter;
wherein the at least one sensor opening is spaced apart from a longitudinal axis $L_A$ of the largely cylindrical portion by a distance $l_{sensoropening}$ and is arranged such that when the apparatus is inserted in an ear canal, the at least one sensor opening contacts an inner wall of the ear canal; the apparatus further comprising:
an ear adapter configured to detachably attach to the largely cylindrical portion, wherein the ear adapter comprises a central piece adapted to engage in the aperture of the largely cylindrical portion;
an ear contact surface adapted to engage with an inner wall of an ear canal when the apparatus is inserted in an ear canal; and
an endpiece adapted to connect the central piece and the ear contact surface, wherein the ear contact surface at least partially encloses the distal end of the tube and is attached thereto such that when the apparatus is inserted into an ear canal, the at least one sensor opening comes to lie in close proximity to an inner wall of the ear canal.

2. The apparatus according to claim 1, wherein the at least one sensor opening is spaced apart from a lateral surface M of the largely cylindrical portion by a distance $m_{sensoropening}$, and wherein $m_{sensoropening}$ is $\leq l_{sensoropening}$.

3. The apparatus according to claim 1, wherein the aperture is a through-aperture.

4. The apparatus according to claim 1, wherein a receiver device adapted for outputting sound signals is integrated in the housing such that the apparatus is adapted to apply sound to an eardrum when the apparatus is inserted in an ear canal, wherein the tube includes a sound outlet opening at the distal end of the tube, and wherein the sound outlet opening is spaced apart from the longitudinal axis $L_A$ of the largely cylindrical portion by a distance $l_{soundoutletopening}$.

5. The apparatus according to claim 4, wherein the receiver device for outputting sound signals and the at least one sensor device adapted to record physiological parameters are designed as an integral component.

6. The apparatus according to claim 4, wherein the sound outlet opening is arranged largely centrally in an end face of the largely cylindrical portion.

7. The apparatus according to claim 1, wherein the ear contact surface is arranged on the largely cylindrical portion such that the at least one sensor opening comes to lie in contact with an inner wall of the ear canal when the apparatus is inserted in an ear canal.

8. The apparatus according to claim 1, wherein at least two sensor devices for recording physiological parameters are designed as an integral component.

9. The apparatus according to claim 1, wherein the tube is designed integral with the housing.

10. The apparatus according to claim 1, wherein the largely cylindrical portion is designed with a convexly curved lateral surface.

11. The apparatus according to claim 1, wherein the ear contact surface is designed with a shape that is largely complementary to the largely cylindrical portion.

12. The apparatus according to claim 1, wherein a longitudinal axis of the ear adapter is spaced apart from the longitudinal axis of the largely cylindrical portion.

13. The apparatus according to claim 1, wherein an end face of the largely cylindrical portion of the distal end of the tube has a radius $R_A$ and a center point $M_A$, and the endpiece of the ear adapter is designed as a circular segment with radius $R_O$ and a center point $M_O$, wherein $R_A < R_O$ and the distance between the center points $M_A$, $M_O$ is $0 < a < R_O$.

* * * * *